(12) United States Patent
Lewis et al.

(10) Patent No.: US 8,518,340 B1
(45) Date of Patent: Aug. 27, 2013

(54) STEAM AUTOCLAVE HAVING CONDENSATE BLEED SYSTEM, AND CONDENSATE DRAINAGE SYSTEM FOR A STEAM AUTOCLAVE

(76) Inventors: Robert W. Lewis, Charlotte, NC (US); Timothy A. Barrett, Douglassville, PA (US)

( * ) Notice: Subject to any disclaimer, the term of this patent is extended or adjusted under 35 U.S.C. 154(b) by 1057 days.

(21) Appl. No.: 11/904,417

(22) Filed: Sep. 27, 2007

(51) Int. Cl.
*A61L 2/00* (2006.01)
*F16K 24/00* (2006.01)

(52) U.S. Cl.
USPC .......................................... 422/295; 137/583

(58) Field of Classification Search
USPC ...................... 137/171, 583, 487.5; 422/295
See application file for complete search history.

(56) References Cited

U.S. PATENT DOCUMENTS

| | | | | |
|---|---|---|---|---|
| 2,605,969 A | * | 8/1952 | Sanders | 236/46 R |
| 3,511,169 A | * | 5/1970 | Jones et al. | 99/370 |
| 3,576,180 A | * | 4/1971 | Michel | 122/406.5 |
| 3,992,984 A | * | 11/1976 | Treiber | 99/330 |

* cited by examiner

*Primary Examiner* — Kevin Joyner
(74) *Attorney, Agent, or Firm* — John F. A. Earley, III; Frank J. Bonini, Jr.; Harding, Earley, Follmer & Frailey, P.C.

(57) ABSTRACT

A steam autoclave has a main drain line and an auxiliary drain line through which condensate in the autoclave chamber is drained, the auxiliary drain line having a conduit extending therethrough defining a path for condensate to move through the auxiliary drain line, and at least a portion of the conduit having a cross-section sized to permit effective draining of condensate through the conduit while the autoclave chamber is pressurized without substantial loss of steam pressure in the autoclave chamber. A sensor may be positioned in the autoclave chamber for sensing a pressure drop during condensate draining while the autoclave chamber is pressurized and for initializing insertion of additional pressurized steam into the autoclave chamber as needed to maintain adequate steam pressure in the autoclave chamber.

30 Claims, 1 Drawing Sheet

STEAM AUTOCLAVE HAVING CONDENSATE BLEED SYSTEM, AND CONDENSATE DRAINAGE SYSTEM FOR A STEAM AUTOCLAVE

BACKGROUND OF THE INVENTION

1. Field of the Invention

The invention relates to steam autoclaves, and more particularly concerns a steam autoclave having a condensate drainage system that provides for condensate drainage while the steam autoclave chamber remains pressurized.

2. Description of the Prior Art

Experimentation has determined that the accumulation of condensation in a conventional steam autoclave is detrimental to the efficiency of autoclave operations. We believe that the accumulated condensate acts as a "heat sink," absorbing thermal energy that, in the absence of the accumulated condensate, would be absorbed by the material being treated (sterilized, for example) in the steam autoclave.

However, opening the drain of conventional steam autoclave to drain accumulated condensate from the steam autoclave chamber while the steam autoclave chamber is pressurized would result in a pressure loss in the steam autoclave chamber that would, in most instances, adversely affect the efficiency of the conventional steam autoclave.

SUMMARY OF THE INVENTION

It is an object of the invention to provide a steam autoclave that permits effective drainage of condensate therefrom while the autoclave chamber is pressurized without any substantial loss of steam pressure in the autoclave chamber.

It is another object to reduce the loss in efficiency associated with build-up of condensate within the steam autoclave.

Another object is to reduce the amount of thermal energy wasted during the operation of a steam autoclave.

These and other objects are accomplished by our invention which is described below.

DETAILED DESCRIPTION

Figure 2:
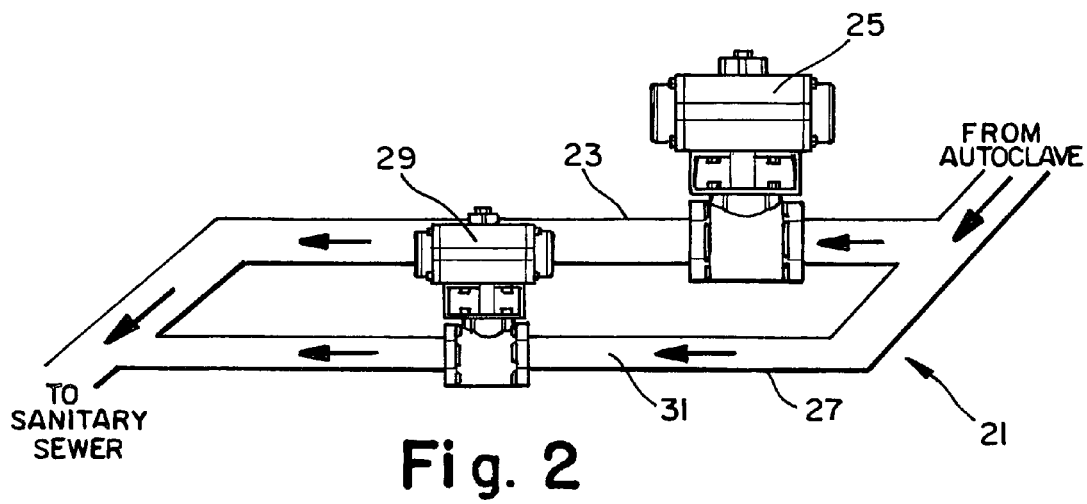
FIG. 2 is a schematic drawing of a condensate drainage system of the steam autoclave shown in FIG. 1.
Figure 1:
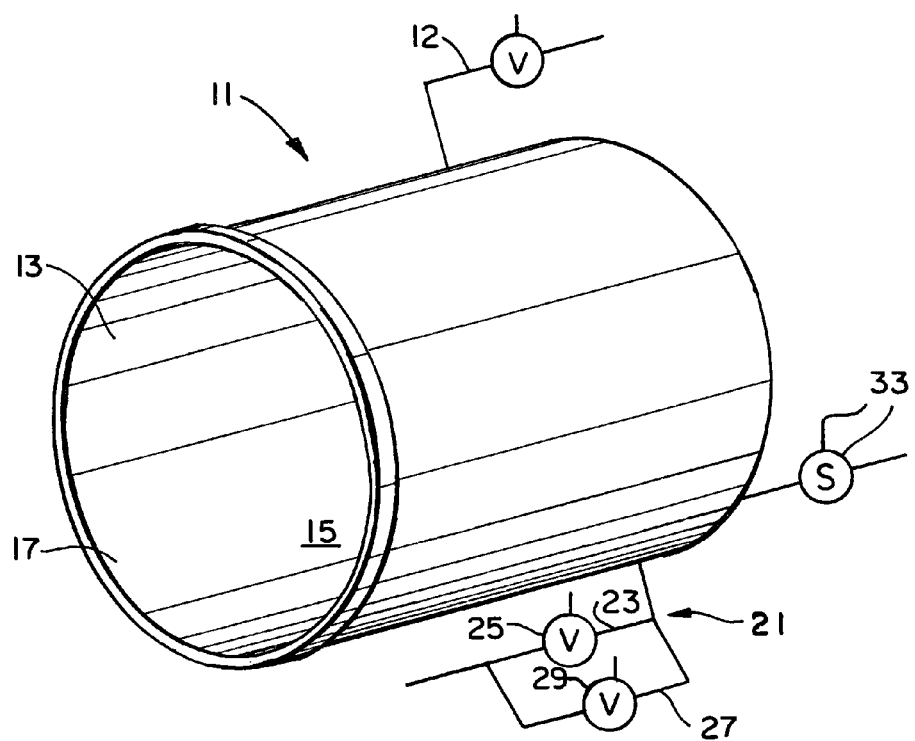
FIG. 1 is a schematic drawing illustrating a steam autoclave constructed in accordance with the invention.

Turning to the drawings, there is shown in FIGS. 1 and 2 a preferred embodiment of our inventive steam autoclave 11 for treating material and objects such as medical waste, medical instruments, tires, airplane parts, etc. The steam autoclave 11, like conventional steam autoclaves, or like the steam sterilization system disclosed in Robert W. Lewis U.S. Pat. No. 6,867,393, which is incorporated herein by reference, has first piping 12 to supply steam to the steam autoclave chamber 13, a steam valve provided along the first piping 12 to control the flow of steam into the steam autoclave chamber 13, preferably a manual isolation valve (preferably a manual ball valve) along the first piping upstream from the steam valve as a safety feature, second piping through which steam is evacuated from the steam autoclave chamber 13, a vacuum pump (when desired) provided along the second piping for evacuating the steam autoclave chamber 13 when desired during the treatment process, and a valve (preferably an electromagnetic solenoid activated valve) provided along a vent portion of the second piping used for venting the steam sterilization chamber 13 to atmosphere. To simplify FIGS. 1 and 2, standard component parts of steam autoclaves such as the above-mentioned steam valve, isolation vale, second piping, vacuum pump when desired, vent portion of the second piping, and the valve along the vent potion of the second piping, are not shown.

The autoclave chamber 13 has an interior 15 where steam treatment (e.g., sterilization) takes place. The steam autoclave chamber 13 has an opening 17 through which access to the interior 15 of the steam autoclave chamber 13 is obtained, and the steam autoclave chamber 13 has a door (not shown) mounted at the opening 17 for sealingly closing the opening 17 against both pressure and vacuum when closed. The door preferably is a full opening hinged door that provides unobstructed access to the steam autoclave chamber 13 when the door is fully opened. The door preferably is equipped with an automatic latching mechanism to seal the door against both pressure and vacuum. Also, the door preferably is equipped with safety interlocks to prevent opening the door until safe pressure and temperature conditions are restored.

A condensate drainage system 21 is provided for draining condensate from the autoclave chamber 13 of the steam autoclave 11. Preferably, as shown in the drawings, the condensate drainage system 21 is provided with a main drain line 23 through which condensate in the autoclave chamber 13 is drained. A main drain valve 25 preferably is mounted in the main drain line 23 for opening the main drain line 23 when desired to drain condensate from the autoclave chamber 13. An auxiliary drain line 27, preferably being in communication with the main drain line 23, also is provided through which condensate in the autoclave chamber 13 is bled (drained) when desired. Preferably, an auxiliary drain valve 29 is mounted in the auxiliary drain line 27 for opening the auxiliary drain line 27 when desired to drain condensate from the autoclave chamber 13.

The auxiliary drain line 27 has a conduit or passageway 31 extending therethrough defining a path for condensate to move through the auxiliary drain line 27. At least a portion of the conduit 31 has a cross-section sized to permit effective draining of condensate through the conduit 31 while the autoclave chamber 13 is pressurized without the occurrence of substantial loss of steam pressure in the autoclave chamber 13. Preferably, the cross-section of the at least a portion of the conduit 31 is in a range of one sixteenth of an inch to one quarter of an inch.

The conduit 31 of the auxiliary drain line 27 may have a cross-section that is constant along the entire length of the auxiliary drain line 27. Alternatively, the conduit 31 may have a restriction formed in it to create a section or portion in the conduit 31 that has a passageway cross-section that is sufficiently sized to permit effective draining of the condensate through the conduit 31 while the autoclave chamber 13 is pressurized without the occurrence of substantial loss of steam pressure in the autoclave chamber 13. Also, alternatively, the conduit 31 may be provided with an oriface plate having and orifice sized to permit effective draining of condensate through the conduit 31 while the autoclave chamber 13 is pressurized without substantial loss of steam pressure in the autoclave chamber 13.

Preferably, a sensor 33 is provided, positioned in the autoclave chamber 13 for sensing a pressure drop during condensate draining while the autoclave chamber 13 is pressurized and for initiating insertion of additional pressurized steam into the autoclave chamber 13 as needed to maintain adequate steam pressure in the autoclave chamber 13.

During operation of the steam autoclave 11, condensate formed in the steam chamber 13 may be drained from the steam chamber 13 as desired while the autoclave chamber 13 is pressurized by opening the auxiliary drain line valve 29, thereby permitting condensate to flow from the steam chamber 13 through the auxiliary drain line 27. Due to the sizing of the cross-section in at least a portion of the conduit 31 being sized to permit effective draining of condensate through the conduit 31 while the autoclave chamber 13 is pressurized without substantial loss of steam pressure in the autoclave chamber 13, condensate may be drained from the steam chamber 13 while the steam chamber 13 is pressurized without a substantial loss of steam pressure in the autoclave chamber 13 occurring.

Moreover, preferably, the steam chamber 13 is provided with the sensor 33 which senses any pressure drop in the steam chamber 13 during condensate draining while the steam chamber 13 is pressurized and initializes insertion of additional pressurized steam into the autoclave chamber 13 as needed to maintain adequate steam pressure in the autoclave chamber 13. Preferably, a controller is provided with the steam autoclave 11 to manage the control functions and system interlocks. The controller preferably controls the steam valves, vent valves, drain valves 25 and 29, and vacuum pump, as well as controlling the insertion of additional pressurized steam into the autoclave chamber 13 as needed to maintain adequate steam pressure in the autoclave chamber 13 in response to a drop in steam pressure sensed by sensor 33.

Alternatively, if the steam feed line (first piping 12) to the autoclave steam chamber 13 is at a constant feed pressure, the steam feed line may be kept open during the operation of the steam autoclave 11, and any loss of pressure due to the auxiliary drain line 27 being open to permit condensate drainage while the steam autoclave chamber 13 is pressurized, is compensated for due to the constant feed pressure from the steam feed line. Accordingly, in this alternative, the sensor 33 may be omitted.

While it is preferred to have the auxiliary drain line 27 in direct communication with the main drain line 23 as illustrated in the drawings, the auxiliary drain line 27 may extend directly from the autoclave chamber 13, rather than extending from the main drain line 23.

In accordance with the invention, a method of retrofitting a conventional steam autoclave is provided. In accordance with the preferred method of retrofitting a steam autoclave, at least a portion of the existing drain line of the conventional steam autoclave 11 is removed and replaced with a condensate drainage system 21, which is shown in FIG. 2 and which comprises a main drain line 23, a main drain valve 25 mounted in the main drain line 23 for opening the main drain line 23, an auxiliary drain line 27, and an auxiliary drain valve 29 mounted in the auxiliary drain line 27 for opening the auxiliary drain line 27. Preferably, fittings are used to connect the condensate drainage system 21 with appropriate piping (e.g., any remaining portion of the original drain line of the conventional steam autoclave being retrofitted) or the conventional autoclave itself.

Alternatively, a hole may be cut into the steam autoclave being retrofitted, a fitting may be attached to the steam autoclave around the hole, and the condensate drainage system 21 (or, alternatively, an auxiliary drain line 27, the auxiliary drain line 27 having an auxiliary drain valve 29 mounted therein for opening the auxiliary drain line 27) may be connected to the fitting.

Preferably, a sensor 33 is positioned (such as by boring into the autoclave chamber, inserting the sensor 33 into the bore such that the sensing portion of the sensor 33 extends into the autoclave chamber of the conventional autoclave being retrofitted, and sealing the bore around the portion of the sensor 33 in the bore) for sensing a pressure drop during condensate draining during operation of the steam autoclave while the autoclave chamber is pressurized and for initializing insertion of additional pressurized steam into the autoclave chamber as needed to maintain adequate steam pressure in the autoclave chamber.

Preferably, the drain valves 25 and 29 and the sensor 33 retrofitted into the conventional steam autoclave are connected to a controller to control when the drain valves 25 and 29 open and close and to control the insertion of additional pressurized steam into the autoclave chamber of the retrofitted steam autoclave as needed to maintain adequate steam pressure in the autoclave chamber in response to a drop in steam pressure sensed by the sensor 33.

The invention claimed is:

1. A regulated medical waste steam autoclave, comprising
   steam autoclave means for sterilizing regulated medical waste, said steam autoclave means including an autoclave chamber,
   a main drain line mounted on the autoclave,
   a main drain valve mounted in the main drain line for opening the main drain line when desired to drain the autoclave chamber,
   an auxiliary condensate drain line through which condensate in the autoclave chamber is drained, and
   an auxiliary drain valve mounted in the auxiliary condensate drain line for opening the auxiliary condensate drain line when desired to drain condensate from the autoclave chamber,
   the auxiliary condensate drain line having a conduit extending therethrough defining a path for condensate to move through the auxiliary condensate drain line, and
   means formed on the auxiliary condensate drain line along at least a portion of the conduit extending therethrough for permitting effective draining of condensate through the conduit while the autoclave chamber is pressurized without substantial loss of steam pressure in the autoclave chamber.

2. The regulated medical waste steam autoclave of claim 1, said means including a cross-section of the at least a portion of the conduit being in a range of one sixteenth of an inch to one quarter of an inch.

3. The regulated medical waste steam autoclave of claim 1, further including
   a sensor positioned in the autoclave chamber for sensing a pressure drop during condensate draining while the autoclave chamber is pressurized and for initializing insertion of additional pressurized steam into the autoclave chamber as needed to maintain adequate steam pressure in the autoclave chamber.

4. The regulated medical waste steam autoclave of claim 1, the autoclave chamber having a lower end portion,
   the main drain line being positioned at and extending downwardly from the lower end portion of the autoclave chamber,
   the auxiliary condensate drain line being in direct communication with the main drain line such that condensate may enter the auxiliary condensate drain line from the main drain line, and
   the auxiliary condensate drain line extending from a portion of the main drain line that is upstream of the main drain valve such that condensate may enter the auxiliary condensate drain line from the main drain line upstream of the main drain valve.

5. The regulated medical waste steam autoclave of claim 1, the autoclave chamber having a lower end portion,
the main drain line being positioned at and extending downwardly from the lower end portion of the autoclave chamber, and
the auxiliary condensate drain line being positioned at and extending downwardly from the lower end portion of the autoclave chamber.

6. The regulated medical waste steam autoclave of claim 1, said means including a restriction formed on at least a portion of the conduit creating a cross-section thereat sized to effectively drain condensate through the conduit while the autoclave chamber is pressurized without substantial loss of steam pressure in the autoclave chamber.

7. The regulated medical waste steam autoclave of claim 1, said means including an orifice plate provided on the conduit having an orifice sized to permit effective draining of condensate through the conduit while the autoclave chamber is pressurized without substantial loss of steam pressure in the autoclave.

8. A condensate drainage system for draining condensate from a regulated medical waste steam autoclave, the regulated medical waste steam autoclave having steam autoclave means for sterilizing regulated medical waste, said steam autoclave means including an autoclave chamber, the condensate being formed in the autoclave chamber during operation of the steam autoclave means for sterilizing regulated medical waste, the condensate drainage system comprising
a main drain line,
a main drain valve mounted in the main drain line for opening the main drain line when desired,
an auxiliary condensate drain line through which condensate formed in the autoclave chamber during operation of the steam autoclave means for sterilizing regulated medical waste is drained,
an auxiliary condensate drain valve mounted in the auxiliary condensate drain line for opening the auxiliary condensate drain line when desired to drain condensate formed during operation of the steam autoclave means for sterilizing regulated medical waste from the autoclave chamber,
the auxiliary condensate drain line having a conduit extending therethrough defining a path for the condensate to move through the auxiliary condensate drain line, and
means formed on the auxiliary condensate drain line along at least a portion of the conduit extending therethrough for permitting effective draining of condensate through the conduit while the autoclave chamber is pressurized without substantial loss of steam pressure in the autoclave chamber.

9. The condensate drainage system of claim 8,
said means including a cross-section of the at least a portion of the conduit being in a range of one sixteenth of an inch to one quarter of an inch.

10. The condensate drainage system of claim 8, further including
a sensor positioned in the autoclave chamber for sensing a pressure drop during condensate draining while the autoclave chamber is pressurized and for initializing insertion of additional pressurized steam into the autoclave chamber as needed to maintain adequate steam pressure in the autoclave chamber.

11. The condensate drainage system of claim 8,
said means including a restriction formed on at least a portion of the conduit creating a cross-section thereat sized to effectively drain condensate through the conduit while the autoclave chamber is pressurized without substantial loss of steam pressure in the autoclave chamber.

12. The condensate drainage system of claim 8,
said means including an orifice plate provided on the conduit having an orifice sized to permit effective draining of condensate through the conduit while the autoclave chamber is pressurized without substantial loss of steam pressure in the autoclave.

13. A regulated medical waste steam autoclave, comprising
steam autoclave means for sterilizing regulated medical waste, said steam autoclave means including an autoclave chamber,
a main drain line mounted on the autoclave,
a main drain valve mounted in the main drain line for opening the main drain line when desired to drain the autoclave chamber,
auxiliary condensate drain line means for draining condensate from the autoclave chamber when the autoclave chamber is pressurized and for maintaining adequate steam pressure in the autoclave chamber while draining condensate from the autoclave chamber while the autoclave chamber is pressurized, and
an auxiliary drain valve mounted in the auxiliary condensate drain line means for opening the auxiliary condensate drain line means when desired to drain condensate from the autoclave chamber.

14. The regulated medical waste steam autoclave of claim 13,
said auxiliary condensate drain line means including
an auxiliary condensate drain line through which condensate in the autoclave chamber is drained, and
the auxiliary condensate drain line having a conduit extending therethrough defining a path for condensate to move through the auxiliary condensate drain line,
at least a portion of the conduit having a cross-section sized to effectively drain condensate through the conduit while the autoclave chamber is pressurized without substantial loss of steam pressure in the autoclave chamber, and
the steam autoclave further including a sensor positioned in the autoclave chamber for sensing a pressure drop during condensate draining while the autoclave chamber is pressurized and for initializing insertion of additional pressurized steam into the autoclave chamber as needed to maintain adequate steam pressure in the autoclave chamber.

15. The regulated medical waste steam autoclave of claim 14,
the cross-section of the at least a portion of the conduit being in a range of one sixteenth of an inch to one quarter of an inch.

16. The regulated medical waste steam autoclave of claim 13,
the autoclave chamber having a lower end portion,
the main drain line being positioned at and extending downwardly from the lower end portion of the autoclave chamber,
the auxiliary condensate drain line means being positioned on and in direct communication with the main drain line such that condensate may enter the auxiliary condensate drain line means from the main drain line, and
the auxiliary condensate drain line means extending from a portion of the main drain line that is upstream of the main drain valve such that condensate may enter the auxiliary condensate drain line means from the main drain line upstream of the main drain valve.

17. The regulated medical waste steam autoclave of claim 13,
the autoclave chamber having a lower end portion,
the main drain line being positioned at and extending downwardly from the lower end portion of the autoclave chamber, and
the auxiliary condensate drain line means being positioned at and extending downwardly from the lower end portion of the autoclave chamber.

18. The regulated medical waste steam autoclave of claim 13,
said auxiliary condensate drain line means including a restriction formed on at least a portion of the conduit creating a cross-section thereat sized to effectively drain condensate through the conduit while the autoclave chamber is pressurized without substantial loss of steam pressure in the autoclave chamber.

19. The regulated medical waste steam autoclave of claim 13,
said auxiliary condensate drain line means including an orifice plate provided on the conduit having an orifice sized to permit effective draining of condensate through the conduit while the autoclave chamber is pressurized without substantial loss of steam pressure in the autoclave.

20. A condensate bleed system for bleeding condensate from a regulated medical waste steam autoclave, the regulated medical waste steam autoclave having steam autoclave means for sterilizing regulated medical waste, said steam autoclave means including an autoclave chamber, the condensate being formed in the autoclave chamber during operation of the steam autoclave means for sterilizing medical waste, the condensate bleed system comprising
a main drain line,
a main drain valve mounted in the main drain line for opening the main drain line when desired to drain the autoclave chamber,
a condensate drain line through which condensate formed in the autoclave chamber during operation of the steam autoclave means for sterilizing regulated medical waste is bled,
a drain valve mounted in the condensate drain line for opening the condensate drain line when desired to bleed condensate formed during operation of the steam autoclave means for sterilizing regulated medical waste from the autoclave chamber, and
the condensate drain line having a conduit extending therethrough defining a path for the condensate to move through the condensate drain line, and
at least a portion of the conduit having a restriction formed therein creating a cross-section thereat sized to effectively drain condensate through the conduit while the autoclave chamber is pressurized without substantial loss of steam pressure in the autoclave chamber.

21. The condensate bleed system of claim 20,
said restriction comprising an orifice plate provided on the conduit having an orifice sized to permit effective draining of condensate through the conduit while the autoclave chamber is pressurized without substantial loss of steam pressure in the autoclave.

22. A condensate bleed system for bleeding condensate from a regulated medical waste steam autoclave, the regulated medical waste steam autoclave having steam autoclave means for sterilizing regulated medical waste, said steam autoclave means including an autoclave chamber, the condensate being formed in the autoclave chamber during operation of the steam autoclave means for sterilizing medical waste, the condensate bleed system comprising
a main drain line mounted on the autoclave,
a main drain valve mounted in the main drain line for opening the main drain line when desired to drain the autoclave chamber,
a condensate drain line through which condensate formed in the autoclave chamber during operation of the steam autoclave means for sterilizing regulated medical waste is bled,
a drain valve mounted in the condensate drain line for opening the condensate drain line when desired to bleed condensate formed during operation of the steam autoclave means for sterilizing regulated medical waste from the autoclave chamber, and
the condensate drain line having a conduit extending therethrough defining a path for the condensate to move through the condensate drain line, and
means formed on the condensate drain line along at least a portion of the conduit extending therethrough for permitting effective draining of the condensate through the conduit while the autoclave chamber is pressurized without substantial loss of steam pressure in the autoclave chamber.

23. The condensate drainage system of claim 22,
said means including a cross-section of the at least a portion of the conduit being in a range of one sixteenth of an inch to one quarter of an inch.

24. The condensate drainage system of claim 22, further including
a sensor positioned in the autoclave chamber for sensing a pressure drop during condensate draining while the autoclave chamber is pressurized and for initializing insertion of additional pressurized steam into the autoclave chamber as needed to maintain adequate steam pressure in the autoclave chamber.

25. The condensate bleed system of claim 22,
said means including a restriction formed on at least a portion of the conduit creating a cross-section thereat sized to effectively drain condensate through the conduit while the autoclave chamber is pressurized without substantial loss of steam pressure in the autoclave chamber.

26. The condensate bleed system of claim 22,
said means including an orifice plate provided on the conduit having an orifice sized to permit effective draining of condensate through the conduit while the autoclave chamber is pressurized without substantial loss of steam pressure in the autoclave.

27. An apparatus, comprising
steam autoclave means for sterilizing regulated medical waste, said steam autoclave means including an autoclave chamber,
a main drain line mounted on the autoclave means,
a main drain valve mounted in the main drain line for opening the main drain line when desired to drain the autoclave chamber,
an auxiliary condensate drain line through which condensate in the autoclave chamber is drained, and
an auxiliary drain valve mounted in the auxiliary condensate drain line for opening the auxiliary condensate drain line when desired to drain condensate from the autoclave chamber,
the auxiliary condensate drain line having a conduit extending therethrough defining a path for condensate to move through the auxiliary condensate drain line, and
at least a portion of the conduit having a restriction formed therein creating a cross-section thereat sized to effectively drain condensate through the conduit while the autoclave chamber is pressurized without substantial loss of steam pressure in the autoclave chamber.

28. An apparatus, comprising steam autoclave means for sterilizing regulated medical waste, said steam autoclave means including an autoclave chamber, a main drain line mounted on the autoclave means, a main drain valve mounted in the main drain line for opening the main drain line when desired to drain the autoclave chamber, an auxiliary condensate drain line through which condensate in the autoclave chamber is drained, and an auxiliary drain valve mounted in the auxiliary condensate drain line for opening the auxiliary condensate drain line when desired to drain condensate from the autoclave chamber, the auxiliary condensate drain line having a conduit extending therethrough defining a path for condensate to move through the auxiliary condensate drain line, and means formed on the auxiliary condensate drain line along at least a portion of the conduit extending therethrough for permitting effective draining of condensate through the conduit while the autoclave chamber is pressurized without substantial loss of steam pressure in the autoclave chamber.

29. The apparatus of claim 28, said means including an orifice plate provided on the conduit having an orifice sized to permit effective draining of condensate through the conduit while the autoclave chamber is pressurized without substantial loss of steam pressure in the autoclave.

30. The apparatus of claim 28, said means including a cross-section of the at least a portion of the conduit being in a range of one sixteenth of an inch to one quarter of an inch.

* * * * *